(12) United States Patent
Hornig et al.

(10) Patent No.: US 7,303,395 B2
(45) Date of Patent: Dec. 4, 2007

(54) DEVICE FOR THE REMOVAL OF TEETH

(76) Inventors: Hans-Peter Hornig, Industriestrasse 10, Bammental (DE) 69245; Thomas Offermann, Nebelhornstrasse 15, Oberstdorf (DE) 87561

( * ) Notice: Subject to any disclaimer, the term of this patent is extended or adjusted under 35 U.S.C. 154(b) by 224 days.

(21) Appl. No.: 10/474,599

(22) PCT Filed: Apr. 10, 2002

(86) PCT No.: PCT/EP02/03988

§ 371 (c)(1),
(2), (4) Date: Oct. 10, 2003

(87) PCT Pub. No.: WO02/083024

PCT Pub. Date: Oct. 24, 2002

(65) Prior Publication Data

US 2004/0126741 A1    Jul. 1, 2004

(30) Foreign Application Priority Data

Apr. 12, 2001 (DE) ................................ 101 18 717
Jul. 27, 2001 (DE) ................................ 101 36 762

(51) Int. Cl.
*A61C 3/14* (2006.01)
*A61C 3/00* (2006.01)

(52) U.S. Cl. ...................... 433/159; 433/152; 433/158
(58) Field of Classification Search ........ 433/152–154, 433/157–162
See application file for complete search history.

(56) References Cited

U.S. PATENT DOCUMENTS

| | | | | |
|---|---|---|---|---|
| 1,110,379 A | * | 9/1914 | Craig | 433/158 |
| 1,666,860 A | * | 4/1928 | Maranda | 433/161 |
| 2,210,349 A | * | 8/1940 | Van Beeck | 433/152 |
| 2,640,266 A | * | 6/1953 | Sarti | 433/152 |
| 2,777,198 A | * | 1/1957 | Wallace | 433/118 |
| 2,977,683 A | * | 4/1961 | Wiltse | 433/98 |
| 4,230,454 A | * | 10/1980 | Lococo | 433/153 |
| 4,443,196 A | | 4/1984 | Rico | 433/158 |
| 5,015,185 A | | 5/1991 | Cane et al. | 433/159 |
| 5,839,896 A | | 11/1998 | Hickok et al. | 433/159 |
| 6,019,602 A | | 2/2000 | Fletcher et al. | 433/152 |

FOREIGN PATENT DOCUMENTS

| | | |
|---|---|---|
| DE | 603210 | 9/1934 |
| DE | 686412 | 4/1937 |
| DE | 3740474 | 6/1989 |

(Continued)

*Primary Examiner*—John J Wilson
(74) *Attorney, Agent, or Firm*—Darby & Darby

(57) ABSTRACT

A divice for the removal of teeth and/or tooth roots from a tooth socket or from a jawbone includes an extractor having a fisrt and second lever and a first and second branch pivotably connected to each other by a hinge, the first branch including a receiving part. A rod for mechanically and manually adjusting the first and second levers is provided. An adjusting part for axially moving the rod relative to the second lever against a force needed to extract a tooth is provided. An extracting part including at least one resistance element is provided for anchorinf the tooth or a tooth stump, the extracting part including a first support for coupling with the receiving part of the first branch. A second support is placed against the extractor and has an openning for the extracting part.

22 Claims, 6 Drawing Sheets

FOREIGN PATENT DOCUMENTS

| | | |
|---|---|---|
| DE | 196 46 097 A1 | 5/1998 |
| DE | 19815133 | 10/1999 |
| EP | 0318709 | 6/1989 |
| FR | 2559053 | 8/1985 |
| FR | 2702648 | 9/1994 |
| GB | 210496 | 2/1924 |
| JP | 1119098 | 1/1999 |

\* cited by examiner

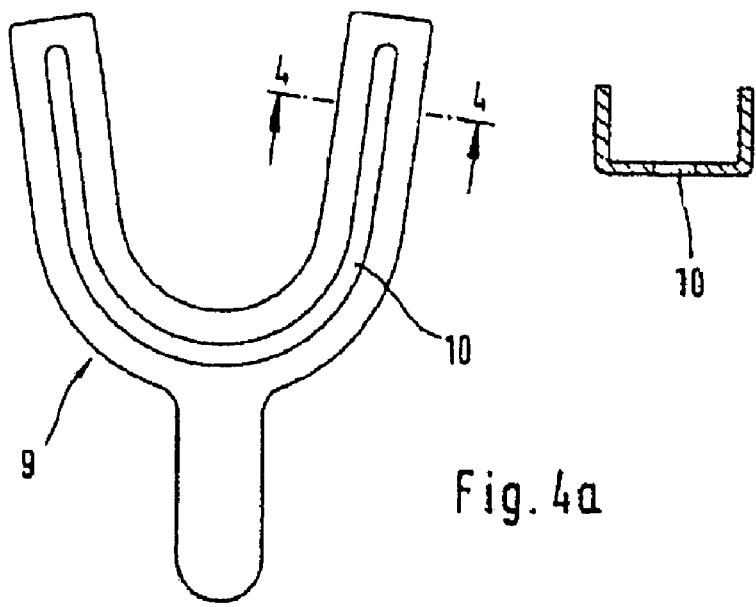
Fig. 5a
Fig. 4a
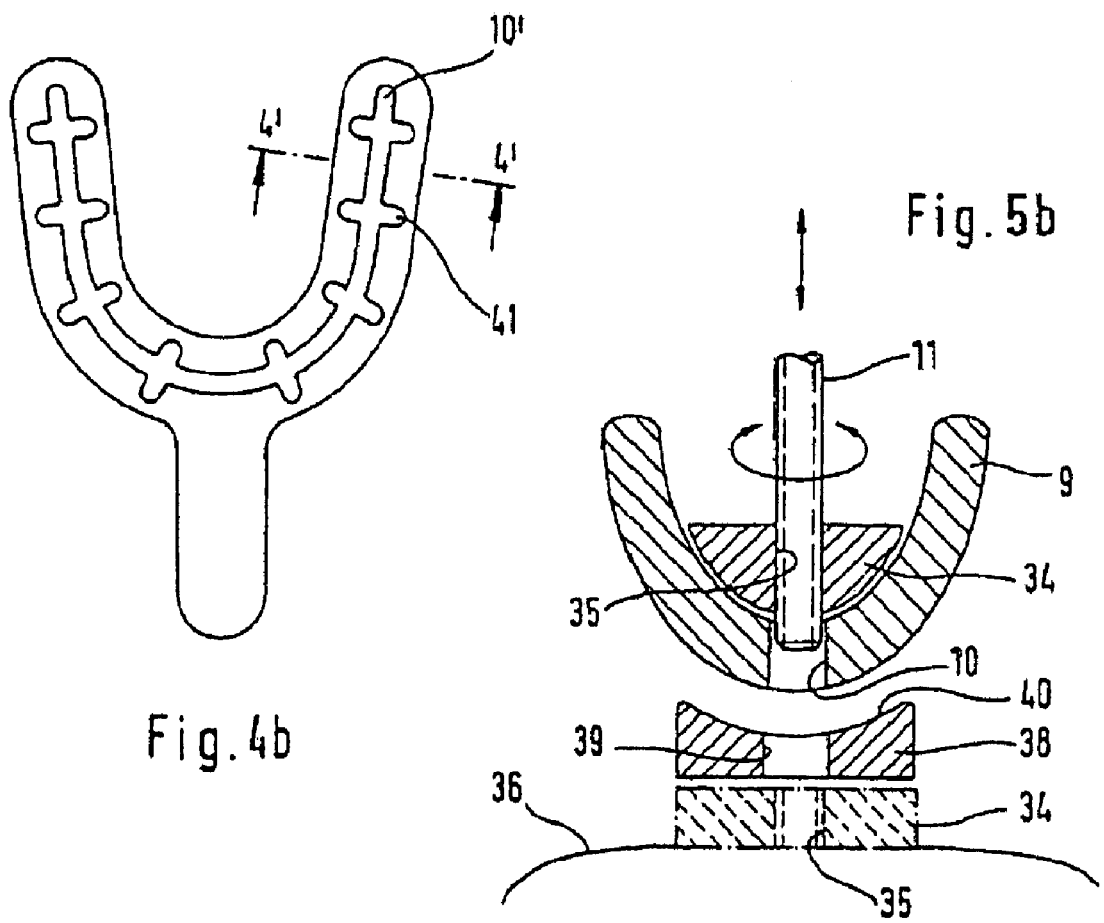
Fig. 4b
Fig. 5b

DEVICE FOR THE REMOVAL OF TEETH

The invention relates to a device for the removal of teeth and/or tooth roots from the tooth socket or from the jawbone by means of an extractor.

BACKGROUND

Devices for the removal of teeth from the tooth socket or jaw such as extracting pliers are already known (DE 198 15 133 A1, DE 686 412 and DE 37 40 474), each of which is equipped with an extractor, consisting of at least one first support that can rest in the oral cavity or on the jawbone ridge or on the top or crown of the tooth and that has at least one opening, of a second support that can rest on the first support and that has a screw part, and of at least one extracting part that extends through the openings of the first and/or at least one second support and that has one or more resistance elements.

The device according to DE 198 15 133 A1 especially has the drawback that, due to the high forces involved, the root screw cannot be moved smoothly out of the tooth bed without causing damage since, when the two lever arms are actuated, the force exerted cannot be appropriately regulated and consequently, the alveolar wall might be damaged during the extraction of the tooth.

SUMMARY OF THE INVENTION

It is an object of the present invention to provide a device for the removal of teeth from the tooth socket or from the jawbone and for its placement into the oral cavity of a patient to be done in such a way that the teeth can be removed without damaging or disproportionately enlarging the tooth socket, so that damage or severe harm to the alveolar wall can be largely avoided.

A device according to the present invention may include the following features:

1.1 the device has an extractor or a plier-like extractor on which an impression tray configured as a support is arranged or to which the impression tray can be connected;
1.2 the support serves to receive a deformable compound or an impression material,
1.3 the impression tray or the support and/or the impression material can rest directly in the oral cavity or on the jawbone ridge or on the top or crown of the tooth,
2.1 the support or the impression tray has at least one opening,
2.2 at least one extracting part or screw part extends through the opening,
2.3 the extracting part is fitted with one or more resistance elements that can be anchored in a tooth or tooth stump,
2.4 the extracting part is also provided with at least one additional support or adjusting part,
3.1 the support or adjusting part can be inserted into a receiving part or into a slit opening,
3.2 the receiving part or the two slit openings are provided in a lever means of the plier-like extractor,
3.3 the two lever means are joined together by a hinge so that they can pivot and each has another lever arm,
3.4 the two lever arms can be configured by means of an adjusting device so as to pivot against the action of a spring element.

Through the advantageous configuration and arrangement of the extractor, the diseased tooth can be readily pulled out of its root bed in the axial direction or in the lengthwise direction of the tooth without enlarging the root bed, so that the latter is suitable for receiving implants without necessitating major follow-up treatment.

For this purpose, it is advantageous for the lever means to be part of a pair of pliers having two levers joined by the hinge and to be followed by two branches which can lie against each other in one position and which move apart when the levers are actuated, thus adjusting the extractor. It is also advantageous for the lever means to be part of a pair of pliers having two levers joined by a hinge, whereby a rod with a thread is connected to the one lever, and it extends through an opening or bore of the second lever, whereby the spring element that pushes the two levers apart is situated between the two levers.

It is likewise advantageous for the pin to have a first resistance element or threaded part that can be inserted into an opening of the tooth and for it to have an adjusting part and/or a second threaded part.

It is also advantageous for the thread of the first and second threaded parts to be configured so as to wind in opposite directions.

Moreover, it is advantageous for the support to be configured in such a way that it can rest on at least two or more teeth located next to the tooth that is to be extracted.

Finally, in a preferred embodiment of the solution according to the invention, it is provided for the support to be designed as a tooth impression tray and to have one or more openings or an oblong hole opening.

It is also advantageous for the tooth impression tray to be made up of a wall part configured as a support and of at least two side parts that delimit the wall part and that match the curvature of the jaw.

In conjunction with the configuration and arrangement according to the invention, it is advantageous for the upper end of the pin to have a coupling part for connecting an adjusting arm.

Furthermore, it is advantageous for the extractor to consist of at least one support that can rest in the oral cavity or on the jawbone ridge or on the tops or crowns of the teeth and of an extracting part or pin that can rest on the support and that has one or more resistance elements that are hook-shaped and/or that prevent friction and/or that can withstand pulling stress, whereby at least one resistance element or a threaded part can be inserted into the interior of the tooth and firmly anchored there.

Moreover, it is advantageous for an adjusting part to be inserted or to act between the extracting part or the pin and the support and, by means of this adjusting part, the pin can be pulled out of the tooth socket, together with the tooth.

It is likewise advantageous for the upper end of the rod to have a coupling part or threaded part for connecting an adjusting part and/or a nut.

Furthermore, it is advantageous for the rod to receive at least one spring element.

In another embodiment of the invention, it is advantageous for the first support or the impression tray to be permanently or detachably arranged on one lever or on one branch and for the extracting part or else the rod to have an adjusting part and/or a locking part by means of which the rod can be actuated.

Finally, it is advantageous for the adjusting part to be configured as a stepping motor that can be made to interact with or drive the rod or the pin and by means of which the tooth can be pulled directly or indirectly out of the tooth socket.

It is also advantageous for the pin to be configured rigidly and to have at least one marking or notch between its upper and lower ends or else two markings arranged at a distance from each other in such a way that they serve as a reference for the path of movement of the tooth out of its socket.

Since the pin is provided with two opposing threads, it can be easily screwed into the tooth or into the tooth canal or root canal and anchored in such a way that the pin can withstand pulling stress. By using a second thread, a locknut can easily be screwed and it can then rest on a support when the pin is turned by means of a crank. The support can advantageously rest on suitable supporting means on the dental enamel or on the jawbone ridge. For this purpose, it is advantageous to provide impression material between the support and the dental enamel. The support then rests on the adjacent teeth via the impression material without excessively stressing them or destroying the dental enamel. If there are no teeth present in the immediate vicinity of the tooth that is going to be pulled, then the impression material can also be shaped in such a way that it can easily rest on the jawbone ridge. In an advantageous manner, the support is configured in such a way that it can also rest on several adjacent teeth. The support can also be configured as an impression tray that matches the curvature of the dentition and that is readily suited to receive the impression material.

In an advantageous manner, the impression tray can be provided with several consecutively arranged bores or with an oblong hole opening into which the pin can be inserted.

For example, in order to attach a lever arm to the upper end of the pin, the latter can have a coupling part or a hexagonal connection onto which a coupling element of a ratchet wrench can be placed. The pitch of the upper thread is selected in such a way that, with the smallest possible application of force, the tooth can be pulled out of the tooth socket. The threaded part can also be advantageously configured as a metric fine screw thread.

Since a nut or a second support with a threaded part can rest on the support, the pin and an already mentioned ratchet wrench can be used to pull out the pin affixed in the tooth—via the first support and via the nut that can rest on the support—upwards in the axial direction of the tooth out of the socket without destroying the latter.

The distance between the upper edge of the tooth and the bottom of the first support is selected here in such a way that there is a sufficient space to pull the tooth out of the tooth socket.

In another embodiment of the invention, it is advantageous for the extractor to consist of at least a first support that has at least one opening and that can rest in the oral cavity or on the jawbone ridge or on the top or crown of the tooth, of a second support that has a screw part and that can rest on the first support, and of at least one extracting part that extends through the openings of the first support and/or at least one second support and that has one or more resistance elements, whereby the first and/or the second support is part of a lever means having at least one opening through which the extracting part extends in such a way that, when the lever means is actuated, at least one resistance element and/or one threaded part, which can be inserted or firmly anchored in the interior of the tooth, moves approximately in the lengthwise direction of the tooth or tooth stump, thereby pulling said tooth or tooth stump out of its socket.

Furthermore, it is advantageous for the marking to be situated on a threadless shaft part of the pin.

As a result of the advantageous arrangement, teeth or also root remnants can be removed without having to exert a great deal of force. The flawless removal of single-root teeth also allows immediate implantation since the alveoli remain largely undamaged. Fractured, single-root teeth can likewise be removed. Moreover, due to the gentle treatment of the alveoli, extraction therapy is possible in orthodontics for children (premolar area). In particular, the simple lever arrangement in conjunction with the adjusting device allows a very careful and—if necessary—measured extraction of the tooth from its root bed, whereby the non-traumatic extraction technique can be performed while retaining all of the soft and hard tissue structures.

This treatment leads to fewer postoperative symptoms, i.e. less pain, reduced swelling, in addition to which the healing is also improved. Thanks to the adjusting device, especially the screws with wing nuts at the end of the lever arm, a very fine regulation of the lever forces can be achieved. Since the upper and the lower lever parts are each provided with a slit-shaped opening, the front end can be placed precisely and quickly onto the root screw. For this purpose, it is advantageous for the front part of the lever to be tapered so that there is also a corresponding placement position on the support or on the impression tray for this purpose.

BRIEF DESCRIPTION OF THE DRAWINGS

Additional advantages and details of the invention are explained based on exemplary embodiments with reference to the drawings. The following are shown.

DETAILED DESCRIPTION

Figure 1:
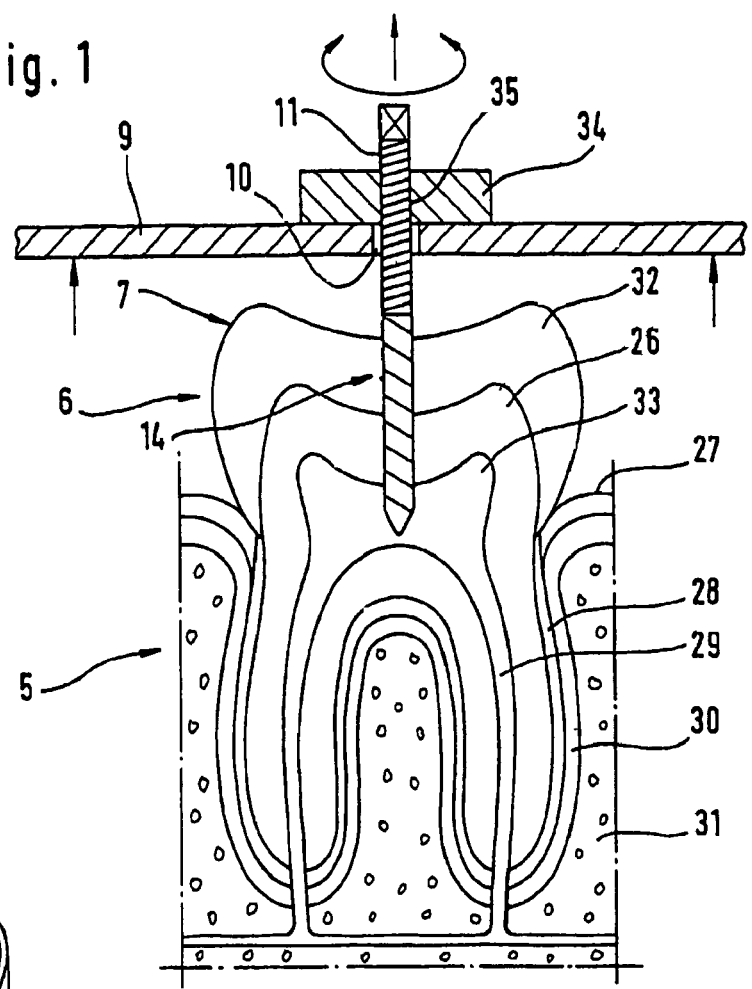
FIG. 1 a schematic representation of a molar, partially in a sectional view with the pin screwed into the molar, and the appertaining support, FIG. 2 a ratchet wrench for adjusting the pin screwed into the tooth that extends through an opening in the support or impression tray for receiving the impression material, FIG. 3 a schematic representation of the extractor that can rest via the impression material on several incisors and a molar, FIGS. 4a, 4b respective embodiments of a tooth impression tray for receiving the impression material, FIGS. 5a, 5b respective sections along lines 4/4 and 4'/4' shown in FIGS. 4a and 4b, respectively FIG. 6 a perspective representation of the closed pliers with two branches configured as levers, whereby an impression tray is touching one branch, with the screwed-in root screw or extracting part, FIG. 7 a representation similar to that of FIG. 6, whereby the pliers are open, FIG. 8 a perspective view of the extracting part or of the root screw before the latter is screwed into the tooth, with a holder and a square wrench.

In the drawing, FIG. 1 shows a schematic representation of a molar 5 in which the dental enamel 32, the dentin 26, the cementum 28, the root canal 29, the periodontium 30, the jawbone 31 and the dental pulp 33 are schematically indicated. In the drawing, as shown in FIG. 1, an extracting part or a pin 11 is screwed into the molar 5. The pin 11 consists of an upper, right-handed thread 16 that can be configured as a metric fine screw thread. The threaded part 16 is followed by another threaded part 17, whose winding is opposite that of the threaded part 16 and which can also be configured as a self-cutting thread and it can be screwed into a bore that has been prepared in the tooth 5 so securely that it can readily withstand the tensile forces that need to be applied in order to pull the tooth 5, without causing the tooth or the dental enamel 32 to break in the process.

Figure 3:
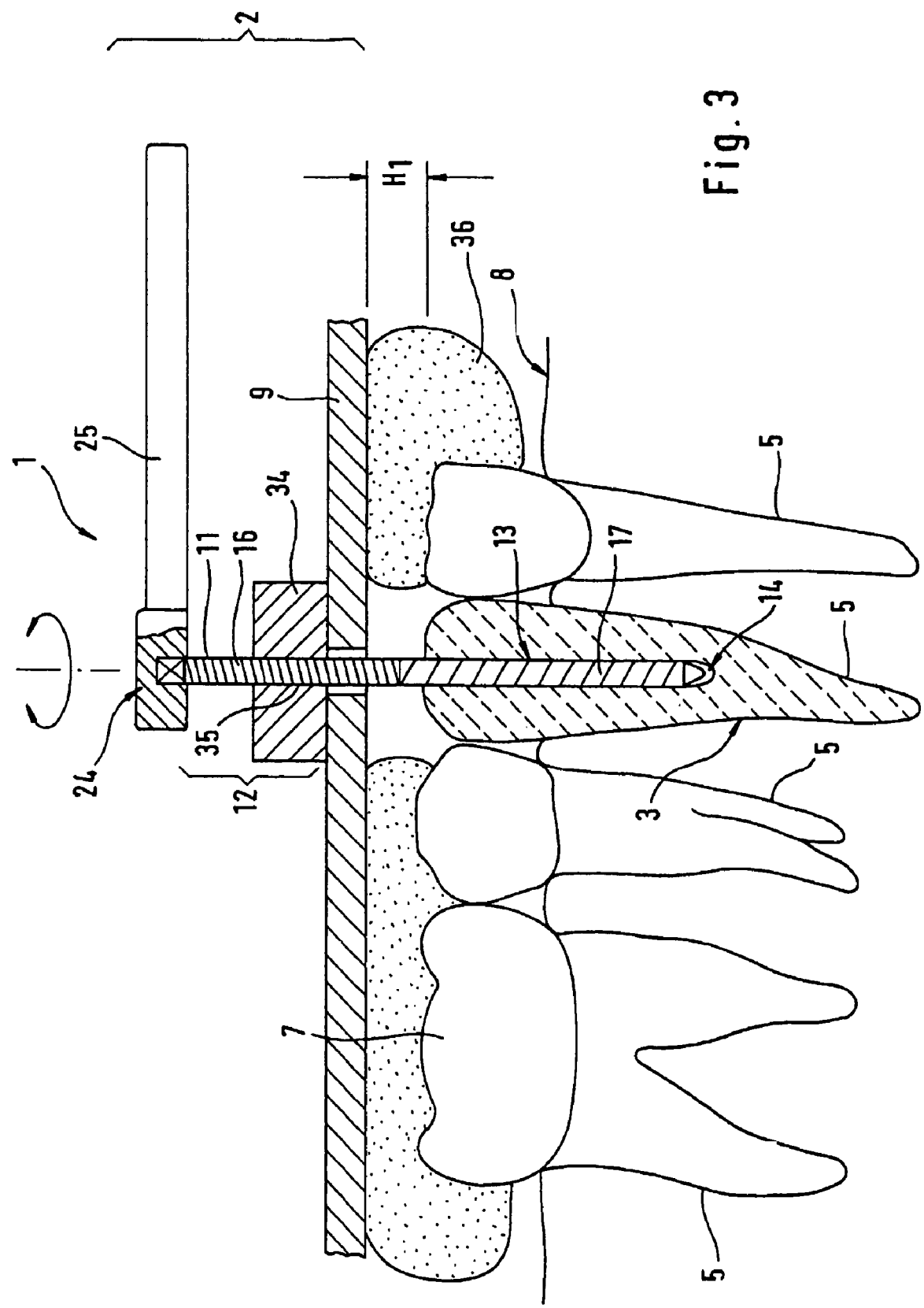

In FIG. 3, for example, the pin 11 is screwed into an incisor, namely, into the root canal 29. The screwed-in depth of the pin 11 depends on how firmly the tooth to be pulled is attached and this depth is selected in such a way that it does not extend into the jawbone 31.

FIG. 1 shows a support 9 that, as shown in FIG. 5, can also be configured as an impression tray for receiving impression material and, for this purpose, can match, for example, the outer contour of the jaw so that the impression tray with the impression material 36 can be placed onto the top of the tooth or the tooth crown 7 in a dimensionally stable way and no impairment or damage to the healthy teeth occurs. If there are no support teeth in the vicinity of the tooth to be pulled, then the possibility also exists to rest the support 9 in another suitable place. In particular, it is advantageous here if the impression material rests on the jawbone ridge of the upper or lower jaw. As shown in FIG. 3, in an advantageous manner, as much impression material is used as is needed to ensure that there is a sufficient distance $H_1$ between the bottom of the support 9 and the tooth crown 7 in order to provide adequate space in the axial direction of the tooth 5 so that said tooth can be pulled out of its socket very precisely without the tooth socket becoming enlarged in the process. Consequently, after follow-up treatment, the tooth socket is readily suitable to receive tooth implants.

The support shown in FIG. 3 can also be configured as a horizontally oriented plate that is provided with a corresponding bore 10 or with numerous consecutively arranged bores or with an oblong opening 10 through which the pin 11 has to pass when it is to receive the support 9.

Figure 2:
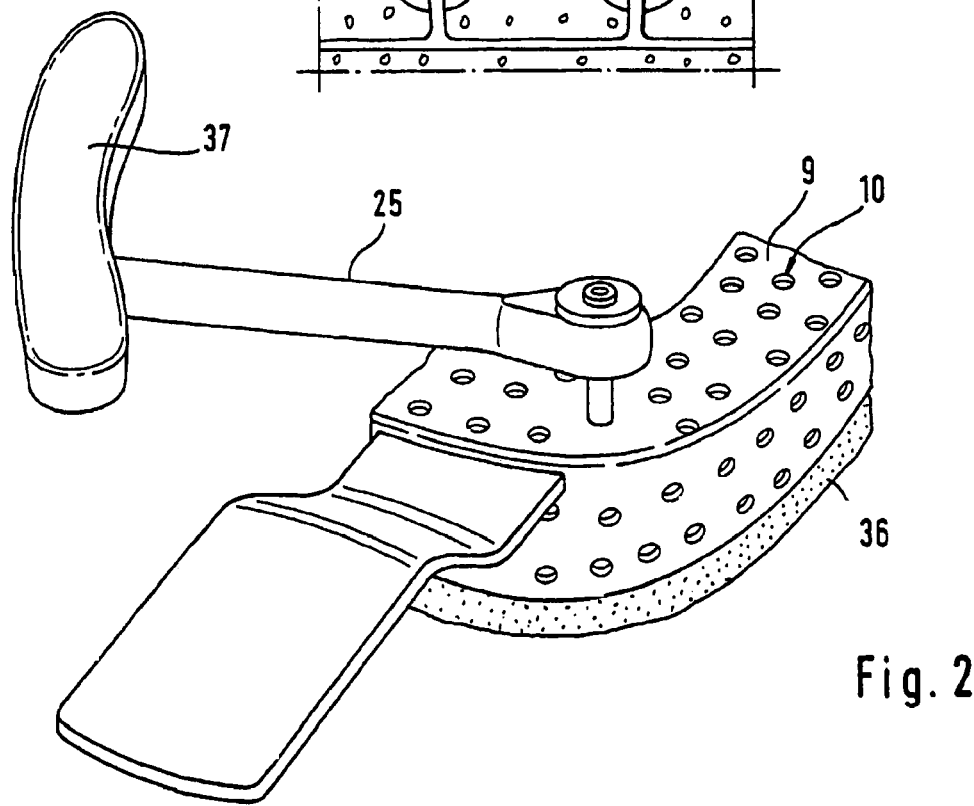

As shown in FIG. 2, the support is placed via a bore 10 onto the pin 11, thus coming to rest, as shown in FIG. 3, on the adjacent healthy teeth 5 or on the molars. Using the ratchet wrench 25, the pin 11 is screwed into the tooth 5 that is to be pulled out. For this purpose, there is a second support 34 on the top of the support 9, said support 34 being provided with a threaded bore 35. When the ratchet wrench 25 is turned, the pin 11 twists out of the support or else the nut 34 twists out upwards, thereby pulling the tooth out of the tooth socket in the axial direction. In this process, the periodontium 30 between the tooth surface or the tooth neck and the tooth socket or jawbone 31 is gradually released. Thus, the tooth does not have to first be loosened as used to be the case, but rather it can gradually be moved in the axial direction by turning the ratchet wrench 25. Thanks to this extraction method, the tooth socket does not become enlarged.

For this purpose, the ratchet wrench 25 is fitted with a coupling part 24 that can be detachably positioned onto a corresponding coupling part provided on the upper end of the pin 11.

Instead of the ratchet wrench 25, the pin 11 can also be actuated by means of a pneumatically or electrically powered motor that is not shown in the drawing. For this purpose, the motor is equipped with a left-hand or right-hand drive so that first of all, it is suited for inserting the pin 11 into the tooth 5 and secondly it offers the possibility that, after the pin 11 has been inserted into the tooth 5, the pin 11 is turned in the opposite direction to the second threaded part 17 and said pin 11 moves the tooth 5 upwards via the support 9. The nut shown in FIG. 3 is integrated into the drive motor for this purpose.

Figure 6:
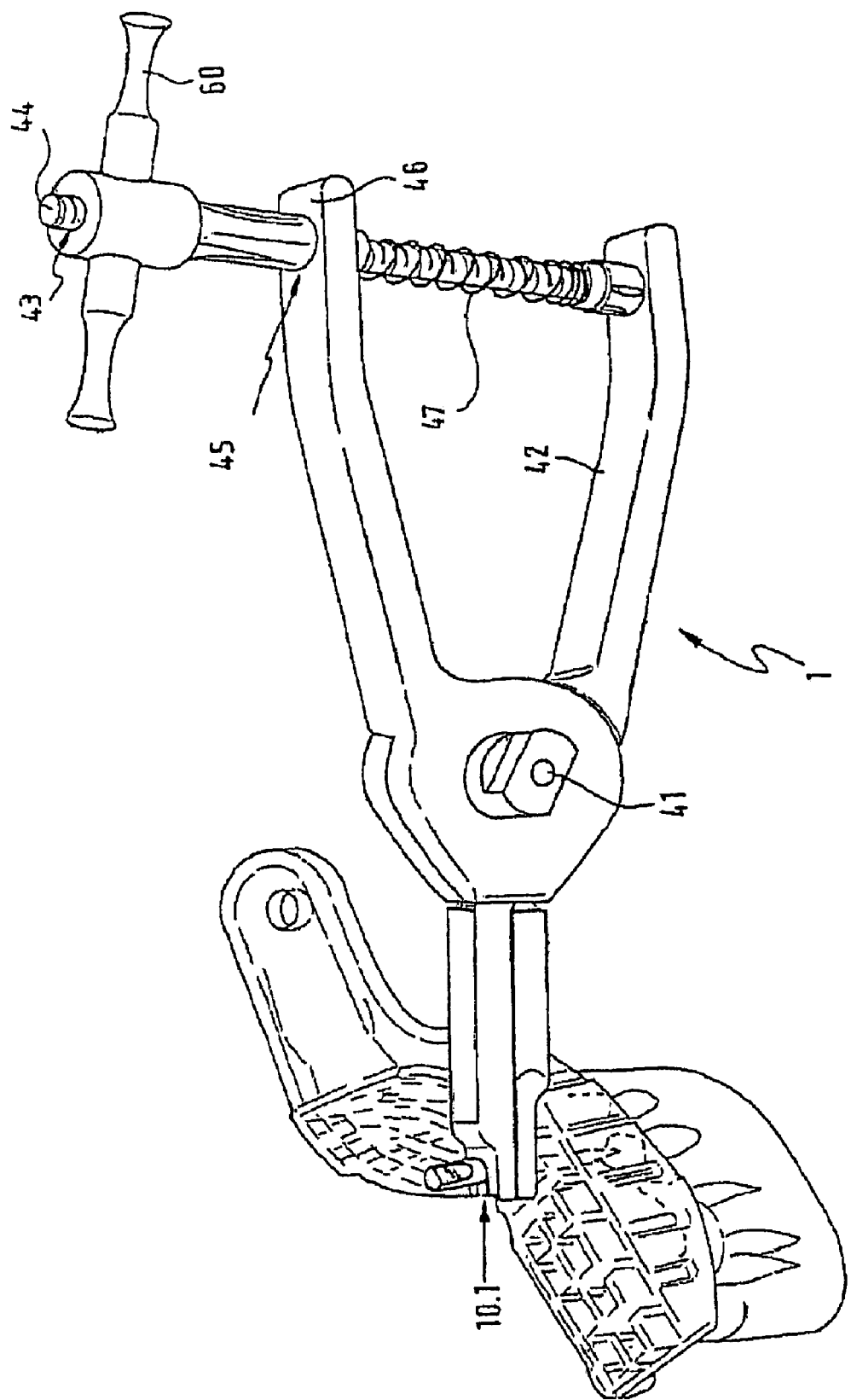
Figure 7:
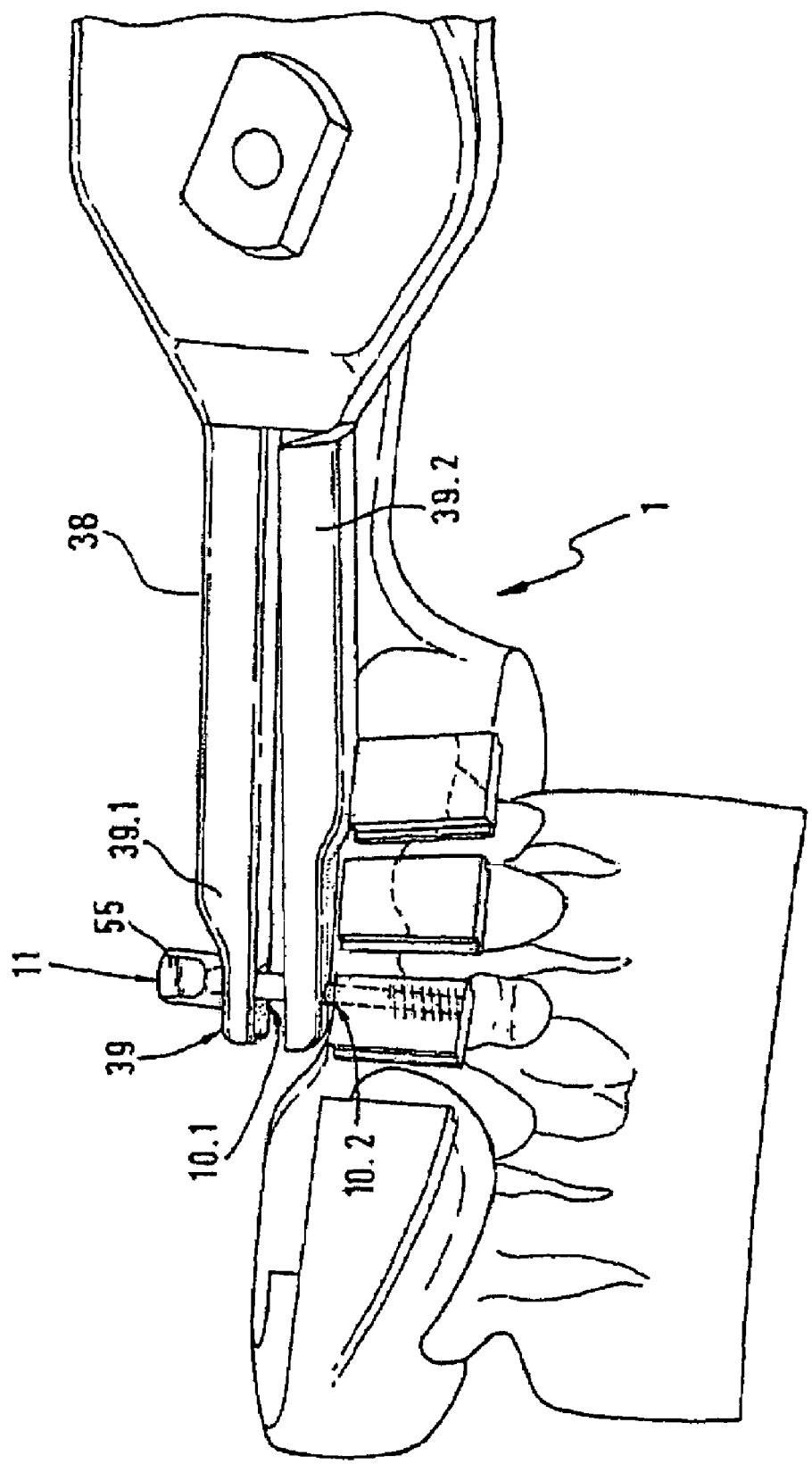

FIGS. 6 and 7 show another embodiment of a device for the removal of teeth 5 and/or tooth roots from the tooth socket 3 or from the jawbone 4 by means of an extractor that is configured as a lever means or as a pair of pliers.

The pliers consist of a first handle 42 and of a second handle 46 that are connected to each other by means of a bolt. Behind the hinge bolt 41, there are two branches 39 that are securely connected to the handles 42 and 46.

Relative to FIG. 6, at the left-hand end of the lever 42, there is a rod 44 that is firmly attached to the lever 42 or else is screwed or welded to it. The rod 44 is arranged perpendicularly on the lever 42 and extends through a bore 45 provided in the lever or handle part 46. On the outer end of the rod 44, there is a thread 43 to receive a screw or nut, for example, a knurled screw or wing nut 60, that can be adjusted by the operator so that the two handle parts 42 and 46 can be moved towards each other and can assume a position as shown in FIG. 6. For this purpose, the wing nut 60 is turned clockwise. If the wing nut 60 is turned counterclockwise, the spring 47 provided on the rod and arranged between the two handle parts 42 and 46 presses the two handle parts 42 and 46 outwards as shown in FIG. 6 so that the two branches 39 can come into contact with each other.

Relative to FIG. 5, the first support 9 or an impression tray 9 is situated on the lower branch 39, and said support 9 rests directly or indirectly on the gum 27 via the dental compound or impression material 36. The impression tray shown in FIG. 5 can be configured similarly to the impression tray shown in FIGS. 2 to 4b.

The impression tray 9 can be detachably or permanently connected to the bottom of the branch 39. For example, it is possible for the impression tray to be screwed or welded to the branch 39.

The impression tray 9 is provided with one or more openings through which the pin or the extraction screw or root screw 11 extend.

Like in the other embodiment, as shown in FIGS. 1 and 3, the extraction screw 11 likewise has resistance elements or barbs or screw elements so that the extraction screw as shown in FIG. 5 can be screwed into the tooth or tooth stump. Here, the extraction screw or pin 11 extends through bores or openings 10 provided in the branches 39, whereby the upper end of the pin 11 projects from the surface of the branch 39.

Figure 8:
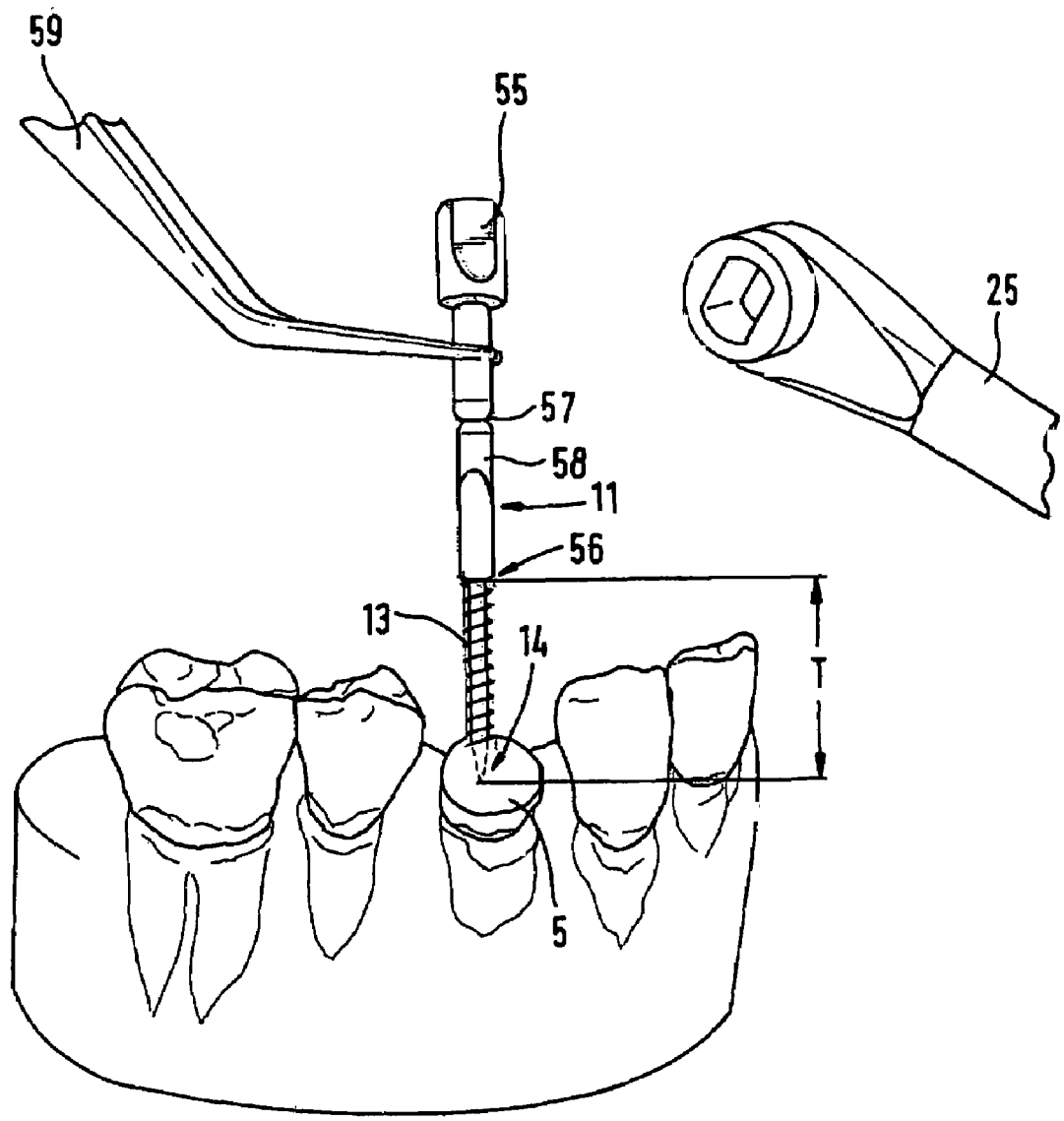

In the embodiment as shown in FIG. 8, the root screw or the extracting part 11 is shown in a perspective view and is screwed into an already provided bore 14 (not shown here) of the tooth 5 by means of the ratchet wrench 25 which, for this purpose, is placed onto an adjusting part or square part 55. The root screw 11 is held in the position shown in FIG. 8 by means of a holder 59 so that the screwing procedure can be carried out more easily. For this purpose, the root screw 11 has a threaded part 13 with a screw-in depth T as shown in FIG. 8. The threaded part 13 is followed by a shaft part 58 with a marking 57 in the upper area. The square part 55 is situated at the upper end of the shaft 58.

The bore 14 in the tooth 5 is selected slightly longer than the screw-in depth T of the root screw 11 so that, during the screwing procedure of the root screw into the bore 14, it is avoided that the lower end of the threaded part 13 strikes the pocket hole part of the bore 14, which could cause the tooth to rupture. For this purpose, in an advantageous manner, a marking ring 56 is provided at the upper end of the threaded part or in the shaft area.

The upper end of the pin 11 can be provided with a thread so that the locking element or a locknut is screwed onto the threaded part of the pin 11, as a result of which, first of all, said locking element secures the pin 11 in the branch 39 and secondly prevents the branch 39 from pivoting beyond its length. At the upper end, the pin 11 can be additionally provided with a hexagon for receiving an adjusting arm 25 or a ratchet wrench. The pin 11 can be screwed into the tooth 5 by means of the ratchet wrench 25.

As can be seen in FIG. 7, the front end of the upper lever or of the branch 39.1 is provided with an oblong hole opening 10.1. The front area of the lower branch 39.2 can also be provided with an oblong hole opening 10.2 so that the two branches 39.1 and 39.2 can be slid onto the cylindrical shaft part 58 crosswise to the longitudinal center axis of the root screw 11 (FIGS. 6 and 7).

According to another embodiment, the upper end of the root screw 11 can be provided with a bore so that the front end of the branch 39.1 can be inserted with a mandrel-like connection part into the corresponding bore of the root screw 11. However, in order to do so, it is necessary for the bore in the root screw 11 to be precisely aligned with the mandrel-like connection element 39.

The handling of the device 1 for the removal of teeth, however, is substantially improved in that both front ends of the branches 39.1 and 39.2 are slit-shaped.

According to the embodiments of FIGS. 6 and 7, a wing nut 60 is screwed onto the upper end of the extracting part or of the root screw 11, and the bottom end of said wing nut comes into contact with the surface of the lever 42 of the device 1 and, by appropriate further adjustment, it moves the lever 46 in the direction of the lever 42, a process in which, as shown in FIG. 7, both branches 39.1 and 39.2 are moved apart and the pin 11 is pulled upwards. The upper branch 39.1 is adjusted until the marking 57 is visible between the two branches 39.1 and 39.2. Then the operator knows that the tooth 5 can be pulled up sufficiently and can thus be removed from its tooth bed.

To summarize, the sequence of steps for using of the device 1 is explained once again below.

For the extraction process of the tooth 5. as shown in FIG. 7, the pliers 38 are placed in the closed state onto the pin 11. The lock or nut 55 provided on the pin 11 readily allows an adjustment of the upper branch 39 as shown in FIG. 6. In other words, when the pliers are actuated, i.e. when the handle 46 moves towards the handle 42, the two branches 39 open and the pin 11 moves in the axial direction along a center line of the rod, that is to say, in the axial direction of the tooth 5. In this manner, the tooth is pulled out of the tooth bed without damaging the gums. The exact movement of the rod 11 is along the a curved trajectory. The direction of movement is shown by the arrow in FIG. 7. Thanks to the slit provided in the branch 39, the rod 11 can also run exactly on its center line so that no lateral pressure is exerted on the tooth 5.

LIST OF REFERENCE NUMERALS

1 device for removal of teeth=pliers
2 extractor
3 tooth socket, alveoli
4 jawbone
5 tooth, tooth stump, root remnant
6 top of tooth
7 crown of tooth
8 jawbone ridge
9 first support, impression tray
10.1 opening, bore (FIG. 2) or slit opening (FIG. 5)
11 extracting part, root screw, pin, extraction screw, root screw
12 threaded part, right-hand thread, resistance element
13 threaded part, left-hand thread, resistance element
14 opening in the tooth
16 thread
17 thread
24 coupling element
25 adjusting arm, ratchet wrench
26 alveolar bone
27 gum
28 cementum
29 root canal
30 periodontium, periodontal membrane
31 jawbone
32 dental enamel
33 dental pulp
34 second support, nut, screw part
35 threaded opening, threaded bore
36 impression material
37 hand
38 lever means, pliers
39 connection element, branch
39.1 upper branch
39.2 lower branch
40 pliers
41 hinge axis, hinge bolt, hinge
42 lever, handle
43 thread
44 rod
45 bore
46 second lever, handle
47 spring element, spring
55 adjusting part, square part, support
56 marking
57 marking
58 shaft part
59 holder
60 adjusting part, wing nut, nut, knurled screw

The invention claimed is:

1. A device for the removal of teeth and/or tooth roots from a tooth socket or from a jawbone, the device comprising:
   a plier-like extractor including first and second opposing handles and a first and a second branch pivotably connected to each other by a hinge in such a manner that the first and second branches pivot apart from each other as the first and second opposing handles pivot closer to each other, the first branch including a receiving part;
   a rod including a thread, the rod being affixed on one side to the first handle and extending through a bore of the second opposing handle;
   a spring element disposed between the first and second opposing handles so as to push the first and second opposing handles apart, the second handle being axially moveable relative to the rod;
   an adjusting pan configured to axially move the rod relative to the second handle against an action of the spring element and against a force needed to extract a tooth;
   an extracting part including at least one resistance element configured to anchor the tooth or a tooth stump, the extracting part including at least a first support configured to couple with the receiving part of the first branch; and
   a second support disposable against the extractor and including at least one opening configured to receive the extracting part, the second support including an impression tray configured to receive a deformable compound, at least one of the impression tray and the deformable compound being disposable directly on at least one of an oral cavity, a jawbone ridge, a top of the tooth and a crown of the tooth.

2. The device as recited in claim 1 wherein the extracting part includes a screw part.

3. The device as recited in claim 1 wherein the receiving part includes a slit opening.

4. The device as recited in claim 1 wherein the first support includes a second adjusting part.

5. The device as recited in claim 1 wherein the deformable compound includes an impression material.

6. The device as recited in claim 1 wherein the adjusting part includes a wing nut.

7. The device as recited in claim 1 wherein the first and second handles and the first and second branches form a pair of pliers joined by the hinge, the first and second branches being disposable in a first position in which the branches are disposed adjacent one another and being movable apart from each other upon an actuation of the first and second handles so as to adjust the extractor.

8. The device as recited in claim 1 wherein:
the first and second handles and the first and second branches form a pair of pliers joined by the hinge; and
the rod extends through an opening of the second handle.

9. The device as recited in claim 1 wherein the at least one resistance element includes a first threaded part of a pin, the first threaded part being insertable into an opening of the tooth.

10. The device as recited in claim 9 wherein the at least one resistance element includes a second threaded part of the pin.

11. The device as recited in claim 9 wherein the pin includes a second adjusting part.

12. The device as recited in claim 1 wherein the at least one resistance element includes a first and a second threaded part of a pin, threads of the first and a second threaded parts being configured to wind in opposite directions.

13. The device as recited in claim 1 wherein the second support is configured to rest on at least two or more second teeth disposed next to the tooth.

14. The device as recited in claim 1 wherein the second support includes an opening.

15. The device as recited in claim 1 wherein the tooth impression tray includes a wall part configured as a support member and at least two side parts delimiting the wall part and matching a curvature of the jaw.

16. The device as recited in claim 1 wherein the first support includes a second adjusting part configured to connect to an adjusting arm.

17. The device as recited in claim 1 wherein an upper end of the rod includes at least one of a coupling part and a threaded part configured to connect to the adjusting part.

18. The device as recited in claim 1 wherein the rod the rod is configured to receive the spring element.

19. The device as recited in claim 1 wherein the second support is at least one of permanently and detachably on at least one of the first and a second handle and the first and a second branch.

20. The device as recited in claim 1 wherein the extracting part includes a second adjusting part configured to actuate the rod.

21. The device as recited in claim 1 wherein the first support includes a rigid pin including at least one of a first marking disposed between an upper and a lower end of the pin and two second markings disposed at a distance from each other so as to provide a reference for a path of movement of the tooth out of a socket thereof.

22. The device as recited in claim 21 wherein the first marking or the second markings are disposed on a threadless shaft part of the pin.

* * * * *